United States Patent [19]

Drizen et al.

[11] Patent Number: 5,952,006
[45] Date of Patent: Sep. 14, 1999

[54] DRUG PREPARATIONS FOR TREATING IMPOTENCY

[75] Inventors: Alan Drizen; Peter Rothbart, both of Ontario, Canada; Gary M. Nath, Bethesda, Md.

[73] Assignee: L.A.M. Pharmaceuticals, LLC, Miami, Fla.

[21] Appl. No.: 08/825,121

[22] Filed: Mar. 28, 1997

Related U.S. Application Data

[63] Continuation-in-part of application No. 08/536,750, Sep. 29, 1995, abandoned, and a continuation-in-part of application No. 08/796,578, Feb. 6, 1997.

[51] Int. Cl.⁶ .......................... A61K 9/14; A61K 31/557
[52] U.S. Cl. .................. 424/488; 424/484; 424/486; 514/54; 514/530; 514/777; 514/781; 514/929; 536/53
[58] Field of Search ................ 424/78.08, 484, 424/486, 488; 514/54, 777, 781, 530, 929, 944; 536/53

[56] References Cited

U.S. PATENT DOCUMENTS

| | | | |
|---|---|---|---|
| 4,127,118 | 11/1978 | Latorre | 600/38 |
| 4,291,015 | 9/1981 | Keith et al. | 514/509 |
| 4,322,433 | 3/1982 | Leslie et al. | 514/509 |
| 4,801,587 | 1/1989 | Voss et al. | 514/248 |
| 4,829,991 | 5/1989 | Boeck | 600/38 |
| 5,017,229 | 5/1991 | Burns et al. | |
| 5,219,885 | 6/1993 | Frolich et al. | 514/530 |
| 5,464,868 | 11/1995 | Frolich et al. | 514/530 |
| 5,488,059 | 1/1996 | Buhl | 514/349 |
| 5,527,893 | 6/1996 | Burns et al. | |
| 5,646,181 | 7/1997 | Fung et al. | 514/506 |
| 5,681,850 | 10/1997 | Frolich et al. | 514/530 |
| 5,686,425 | 11/1997 | Lee | 514/21 |
| 5,708,031 | 1/1998 | Scott | 514/573 |

FOREIGN PATENT DOCUMENTS

| | | |
|---|---|---|
| 0 266 968 | 5/1988 | European Pat. Off. . |
| 0 346 297 | 12/1989 | European Pat. Off. . |
| 92/03141 | 3/1992 | WIPO . |
| WO 93/00894 | 1/1993 | WIPO . |

OTHER PUBLICATIONS

Chemical Abstracts, 115: 263480, 1991.

*Primary Examiner*—Robert H. Harrison
*Attorney, Agent, or Firm*—Gary M. Nath; Nath & Associates

[57] ABSTRACT

Topical gelled compositions comprising a drug for treating impotency dispersed within a polymer matrix and treatments using the complex.

14 Claims, No Drawings

DRUG PREPARATIONS FOR TREATING IMPOTENCY

RELATED APPLICATIONS

This application is a continuation-in-part of U.S. patent application Ser. No. 08/536,750 filed Sep. 29, 1995, abandoned, and a continuation in part of U.S. patent application Ser. No. 08/796,578 filed Feb. 6, 1997, the entire contents of both applications being incorporated herein by reference in their entirety.

FIELD OF THE INVENTION

This invention relates to the preparation of a transdermal delivery system. The preparation is designed to deliver therapeutic levels of a drug for treating impotency to specific sites below the dermal level of the skin.

DESCRIPTION OF THE PRIOR ART

Over the years, methods have been developed to achieve the efficient delivery of a therapeutic drug to a mammalian body part requiring pharmaceutical treatment. Use of an aqueous liquid which can be applied at room temperature as a liquid but which forms a semi-solid gel when warmed to body temperature has been utilized as a vehicle for some drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC® polyols are used in aqueous compositions to provide thermally gelling aqueous systems. Adjusting the concentration of the polymer provides the desired sol-gel transition temperature, that is, the lower the concentration of polymer, the higher the sol-gel transition temperature, after crossing a critical concentration minimum, below which a gel will not form In U.S. Pat. Nos. 4,474,751 and 4,478,822 drug delivery systems are described which utilize thermosetting gels; the unique feature of these systems is that both the gel transition temperature and/or the rigidity of the gel can be modified by adjusting the pH and/or the ionic strength, as well as by the concentration of the polymer.

Other patents disclosing pharmaceutical compositions which rely upon an aqueous gel composition as a vehicle for the application of the drug are U.S. Pat. Nos 4,883,660; 4,767,619; 4,511,563; 4,861,760; and 5,318,780. Thermosetting gel systems are also disclosed for application to injured mammalian tissues of the thoracic or peritoneal cavities in U.S. Pat. No. 4,911,926.

Ionic polysaccharides have been used in the application of drugs by controlled release. Such ionic polysaccharides as chitosan or sodium alginate are disclosed as useful in providing spherical agglomerates of water-insoluble drugs in the Journal of Pharmaceutical Sciences, Volume 78, Number 11, November 1989, Bodmeier et al. Calcium alginate gel formulations have also found use as a matrix material for the controlled release of herbicides, as disclosed in the Journal of Controlled Release, (1986), pages 229–233, Pfister et al.

In U.S. Pat. No. 3,640,741, a molded plastic mass composed of the reaction product of a hydrophilic colloid and a cross-linking agent such as a liquid polyol, also containing an organic liquid medium such as glycerin, is disclosed as useful in the controlled release of medication or other additives. The hydrophilic colloid can be carboxymethyl cellulose gum or a natural alginate gum which is cross-linked with a polyol. The cross-linking reaction is accelerated in the presence of aluminum and calcium salts.

In U.S. Pat. No. 4,895,724, compositions are disclosed for the controlled release of pharmacological macromolecular compounds contained in a matrix of chitosan. Chitosan can be cross-linked utilizing aldehydes, epichlorohydrin and benzoquinone.

In U.S. Pat. No. 4,795,642, there are disclosed gelatin-encapsulated, controlled-release compositions for release of pharmaceutical compositions, wherein the gelatin encloses a solid matrix formed by the cation-assisted gellation of a liquid filling composition incorporating a vegetable gum together with a pharmaceutically-active compound. The vegetable gums are disclosed as polysaccharide gums such as alginates which can be gelled utilizing a cationic gelling agent such as an alkaline earth metal cation.

While the prior art is silent with respect to aqueous drug delivery vehicles and isotonicity thereof, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are-enclosed by semipermeable membranes so as to allow the fluids within the chambers to diffuse into the environment into which the osmotic drug delivery system is in contact. The drug delivery device can be sized for oral ingestion, implantation, rectal, vaginal, or ocular insertion for delivery of a drug or other beneficial substance. Since this drug delivery device relies on the permeability of the semipermeable membranes to control the rate of delivery of the drug, the drugs or other pharmaceutical preparations by definition, are not isotonic with mammalian blood.

Pharmacological erection therapy is an effective method to treat male erectile dysfunction. The medications most commonly used have been papaverine hydrochloride, a smooth muscle relaxant, and phentolamine mesylate, an α-adrenergic blocker. Recent data have suggested that prostaglandin E1 either alone or in combination with papaverine produces an improved erectile response. To date, however, there have been little objective data comparing the relative efficacy of these medications either alone or in combination. Furthermore, the use of these drugs has required special applicators, which besides being cumbersome, are also painful to use.

A need thus exists for the administration of active therapeutic agents that can be applied topically and transported through the skin or administered by injection without the concommittant presence of pain.

SUMMARY OF THE INVENTION

The present invention relates to the formation of a gelled composition and its use in treating impotency, or erectile dysfunction. More particularly, this invention relates to a composition containing a therapeutic drug for treating impotency, which comprises: a polymer matrix composed of a highly negative charged polymer material which may be selected from the group consisting of polysulfated glucosoglycans, glycosaminoglycans, mucopolysaccharides and mixtures thereof, and a nonionic polymer which may be selected from the group consisting of carboxymethylcellulose sodium, hydroxyethyl cellulose, hydroxypropyl cellulose, and mixtures thereof.

Another embodiment of this invention involves a method for the treatment of impotency in male animals, which comprises applying either topically or by injection into the corpus cavernosa therapeutically effective doses of a gelled suspension of a composition comprising an anti-impotency drug dispersed within a polymer matrix which is suspended in a liquid medium. Preferably, one of the polymer materials has a mean average molecular weight below about 800,000, and the other polymer is a nonionic cellulose derivative. The present invention utilizes a novel combination of polymers each having a specific ionicity. More specifically, the polymers used in the formulation are of two basic types: those which have a strong negative charge, and those which are non-ionic or have no charge attached to them.

DETAILED DESCRIPTION OF THE INVENTION

It has been unexpectedly discovered that an effective therapeutic level of a drug may be administered topically and transdermally delivered through the skin into various sites where the drug is therapeutically effective. In order for this to be accomplished, it has been discovered that the active drug must be suspended or entrapped in a specially designed polymer matrix containing a specific molar ratio of negatively charged polymers and a non-ionic polymer suspended or dissolved in water and solubilizers.

This system is believed to form a matrix which microencapsulates, suspends, and/or entraps the active drug entity such that when it is administered, it is slowly released into the systemic circulatory system or muscular tissue providing a method of delivering an active drug to an affected site in the body through the skin.

The molar ratio of the polymers present in the matrix is critical in this invention. It has been found that molar ratios of the negatively charged polymer to the non-ionic polymer must be from 1:0.5 to 4, and preferably from 1:0.5 to 2.0, and most preferably from 1:0.7 to 2.5. For transdermal delivery of drugs, it has been found that ratios either higher or lower than these levels will result in a polymer shearing effect which produces unacceptable turbulence and air pockets in the composition with resulting loss of potency and efficacy. Furthermore, the solutions tend to separate and form distinct polymer layers when ionic molarity is not appropriate.

At least one of the polymers used to form the matrix of this invention must be sufficiently negatively charged to aid in the dispersion, encapsulation or solubilization of the drug. Particularly preferred polymers which have mean average molecular weights below about 800,000 and preferably molecular weights between 650,000 to 800,000 have been found acceptable to form usable polymer matrixes for transdermal delivery. Polymers with mean average molecular weights between 700,000 and 775,000 are most preferred. Polymers having molecular weights above about 800,000 form solid gels in solution and are unable to serve as part of a transdermal delivery system. Furthermore, the polymers must be sterilizable and be stable during sterilization so that the polymer does not lose molecular weight once formulated into the final transdermal delivery form.

Exemplary, non-limiting examples of compounds that may be used as a source of this molecular weight polymer include polysulfated glucosoglycans, glycosaminoglycans, and mucopolysaccharides, derivatives thereof and mixtures thereof. Particularly preferred mucopolysaccharides are chondroitin sulfate and hyaluronic acid salts. Exemplary hyaluronate salts include sodium, calcium, potassium and magnesium salts with hyaluronate sodium being most preferred.

Hyaluronic acid (HA) occurs naturally in joint synovial fluid, where it plays a lubricating role, and may have biological activity was well. HA is a mucopolysaccharide, and may alternatively be referred to as glycosamfnoglycan. The repeating unit of the hyaluronic acid molecule is a disaccharide consisting of D-glucuronic acid and N-acetyl-D-glucosamine. Because hyaluronic acid possesses a negative charge at neutral pH, it is soluble in water, where it forms highly viscous solutions. The D-glucuronic acid unit and N-acetyl-D-glucosamine unit are bonded through a glycosidic, beta (1-3) linkage, while each disaccharide unit is bonded to the next disaccharide unit through a beta (1-5) linkage. The (beta 1-4) linkages may be broken through hydrolysis with the enzyme hyaluronidase.

A variety of substances, commonly referred to as hyaluronic acid, have been isolated by numerous methods from various tissue sources including umbilical cords, skin, vitreous humour, synovial fluid, tumors, haemolytic streptocci pigskin, rooster combs, and the walls of veins and arteries. It is also being synthesized artificially and by recombinant technology.

Conventional methods for obtaining hyaluronic acid results with a product having differing properties and a wide range of viscosities. U.S. Pat. No. 2,585,546 to Hadian, discloses an example of a method for obtaining hyaluronic acid and which involves extracting acetone-washed umbilical cords with a dilute salt solution, acidifying the resulting extract, removing the clot so formed, precipitating some hyaluronic acid with protein from the acidified extract with ammonium sulfate, agitating the liquid with pyridine, precipitating another fraction highly contaminated with protein, followed by more ammonium sulfate which forces some pyridine out of solution along with the high viscosity hyaluronic acid. The hyaluronic acid collects at the interface between the two liquid phases and may be separated by filtration, centrifugation or another usual procedure. A modification of this process involves the fractionation of the acidic salt extract from umbilical cords with alcohol and ammonium sulfate. Alcohol is added to the acidic salt extract, and the resulting precipitate is removed. Solid ammonium sulfate is added to the liquid until saturation and the solution forms two phases with a precipitate of hyaluronic acid at the interface.

U.S. Pat. No. 4,517,296 to Bracke et al. is directed to the preparation of hyaluronic acid in high yield from Streptococcus bacteria by fermenting the bacteria under anaerobic conditions in a $CO_2$ enriched growth medium, separating the bacteria from the resulting broth and isolating the hyaluronic acid from the remaining constituents of the broth. Separation of the microorganisms from the hyaluronic acid is facilitated by killing the bacteria with trichloroacetic acid. After removal of the bacteria cells and concentration of the higher molecular weight fermentation products, the hyaluronic acid is isolated and purified by precipitation, resuspension and reprecipitation.

One particular fraction of hyaluronic acid (HA) that exhibits excellent matrix formation according to the present invention is hyaluronate sodium having a mean or average molecular weight between 650,000–800,000, preferably 700,000–775,000 with a high degree of purity, 95–100% free, and preferably at least 98% pure, from contamination of related mucopolysaccharides. Furthermore, this hyaluronic acid has a sulphated ash content of less than 15% and a protein content of less than 5%. Examples of usable base salts include those safe from animal and human use, such as sodium, potassium, calcium, and magnesium salts or the like.

In contrast to HA, chondroitins are mucopolysaccharides comprising repeating units of D-glucuronic acid and N-acetyl-D-galactosamine. Chondroitin sulphates are important components of cartilage and bone and are excellent for preparing the polymer matrix herein.

The negative charged polymers are generally present in the system in amounts which enable a solid gel to be formed. Generally, gels are formed using amounts of about 2.0 to about 3.0% by weight with amounts of about 2.1 to about 2.5% by weight being preferred for use as a topical gel.

The solutions used to prepare the gels of the present invention may be prepared in a variety of ways. For example, the polymers may be dissolved in water and purified either separately or jointly and then the optional active drug added to the system.

A particularly preferred procedure involves separately dissolving the nonionic polymer in water and centrifuging the material to form a solution and remove impurities. This may be conveniently done at rotation speeds of 2000 rpm for times of about 30 minutes to about two hours.

In contrast, the negative charged polymer may be blended and stirred in water until it is dissolved. This process must be done while avoiding the formation of bubbles and while freeing the polymer of its electrostatic activity. Furthermore, the molecular weight of the polymer must not be significantly changed during processing and as such mild process conditions are required. Processing conditions of 400–3000 rpm for durations of 16–24 hours have been found acceptable to produce stable solutions or gels of the charged polymer.

Conventional pharmaceutically acceptable emulsifiers, suspending agents, antioxidants (such as sodium metabisulfate) and preservatives (such as benzyl alcohol) may then be added to this system. Once all the components are blended together, such as by mixing 400–3000 rpm for one to four hours, the system is filled into tubes and sterilized. The resulting system is a clear gel which is storage stable for several years.

The drug may be added to the homogenous solution or gel separately once dissolved or disbursed in water. Emulsifiers, suspending agents and preservatives may then be added to this system. One particularly nonlimiting effective material for solubilizing water insoluble drugs is methoxypolyethylene glycol (MPEG) Once all the components are blended together, for 400–3000 rpm for 1 to 4 hours, the system is filled into tubes and sterilized. The resulting system is storage stable for several years.

The formulations may be used topically and also contain conventional pharmaceutically acceptable excipients well known to those skilled in the art, such as surfactants, suspending agents, emulsifiers osmotic enhancers, extenders and dilutants, pH modifiers as well as fragrances, colors, flavors and other additives.

As indicated above, the active drug agents may be blended with the aqueous polymer matrix at the time of manufacture. As such, the drug when in the form of a water-soluble solid is simply diluted with sterilized water or polymer matrix solution and prepared in gel form.

The dosage system can be formed with or without the use of pharmaceutically acceptable preservatives. A significant advantage of the dosage form of the present system relates to its ability to allow the drug to slowly diffuse through tissue when administered thus allowing for an effective therapeutic dose to be present for long periods of time, i.e., 15 minutes to several hours.

In this regard, it should be noted that reference to therapeutically effective dose does not necessarily relate to conventional dosage levels, but does relate to drug levels that achieve an effective therapeutic level at the dose employed, which may be the same level but not at the same frequency of administration previously required for drugs taken orally or by injection. This not only significantly reduces the number of doses required to achieve the same effect, but it also reduces costs, maintenance and health hazards associated with conventional treatment therapies.

Doses may vary from patient to patient depending on the type and severity of the condition being treated and the drug being administered. Generally, doses of 150 mcg to 1000 mcg may be administered with preferred doses using 200 to 500 mcg of drug disbursed in the gelled matrix system. The total dosage of the gelled matrix with drug is usually 0.5 ml to 5 ml in volume.

It is generally recognized that primary erectile dysfunction is almost always due to intrapsychic factors. In rare cases, biogenic factors, usually associated with low testosterone levels and reflecting disorders of the hypothalamic-pituitary-gonadal axis, provide the major etiology. Occasionally, vascular abnormalities are found. Physical factors include systemic diseases (e.g., diabetes mellitus [the most common], syphilis, alcoholism, drug dependency, hypopituitarism, and hypothyroidism); local disorders (e.g., congenital abnormalities na inflammatory diseases of the genitalia); vascular disturbances such as aortic aneurysm and atherosclerosis (edg., Leriche's syndrome); neurogenic disorders (e.g., multiple sclerosis, spinal cord lesions, pituitary micfroadenoma with hyperprolactinemia, and cardiovascular accident); drugs such as hypertensives, sedatives, tranquilizers, and amphetamines; and surgical procedures such as sympathectomy, prostatectomy and castration produce varying effects. Impotence is usually not induced by transurethral prostatectomy, whereas it almost always occurs after perineal prostatectomy. However, retrograde ejaculation is produced in the vast majority of men, irrespective of the type of prostatectomy.

Pharmacological erection therapy is an effective method to treat male erectile dysfunction. The medications most commonly used have been papaverine hydrochloride, a smooth muscle relaxant, and phentolamine mesylate, an α-adrenergic blocker. Recent data have suggested that prostaglandin E1 either alone or in combination with papaverine produces an improved erectile response.

There currently is increasing evidence that prostaglandin E1 is presently the single most effective agent for pharmacological erection therapy. Prostaglandin E1 is a physiological agent that is metabolized locally within the cavernous tissue and there appears to be a low incidence of corporeal fibrosis, priapism or systemic reactions associated with its use. Several studies using subjective evaluation have shown that prostaglandin E1 is more effective than a combination of papaverine and phentolamine. Lee et al found that two-thirds of the men who failed prior intracavernous therapy with papaverine and phentolamine achieved adequate erections with prostaglandin E1. Prostaglandin E1 has also been found to be extremely effective as a single agent in several other studies. Liu et al recently reported that prostaglandin E1 is at least as effective as papaverine in increasing penile blood flow measured by duplex sonography. Prostaglandin E1 has the advantage over papaverine of a slower onset, longer maintenance and less chance of priapism.

Despite these advantages, however, prostaglandin E1 is associated with a significant incidence of penile discomfort.

Prostaglandin E1 is a naturally occurring acidic lipid that is synthesized from fatty acid precursors by most mammalian tissues and has a variety of pharmacologic effects. Human seminal fluid is a rich source of prostaglandins, including $PGE_1$ and $PGE_2$, and the total concentration of prostaglandins in ejaculate has been estimated to be approximately 100–200 mcg/mL. In vitro, alprostadil ($PGE_1$) has been shown to cause dose-dependent smooth muscle relaxation in isolated corpus cavernosum and corpus spongiosum preparations. Additionally, vasodilation has been demonstrated in isolated cavernosal artery segments that were pre-contracted with either norepinephrine or prostaglandin $E_{2\alpha}$. The vasodilatory effects of alprostadil on the cavernosal arteries and the trabecular smooth muscle of the corpora cavernosa result in rapid arterial inflow and expansion of the lacunar spaces within the corpora. As the expanded corporal sinusoids are compressed against the tunica albuginea, venous outflow through subtunical vessels is impeded and penile rigidity develops. This process is referred to as the corporal veno-occlusive mechanism.

The most notable systemic effects of alprostadil are vasodilation, inhibition of platelet aggregation, and stimulation of intestinal and uterine smooth muscle. Intravenous doses of 1 to 10 micrograms per kilogram of body weight lower blood pressure in mammals by decreasing peripheral resistance. Reflex increases in cardiac output and heart rate may accompany these effects.

Alprostadil is rapidly metabolized locally by enzymatic oxidation of the 15-hydroxyl group to 15-keto-$PGE_1$. The enzyme catalyzing this process has been isolated from many tissues in the lower genitourinary tract including the urethra, prostate, and corpus cavernosum. 15-keto-$PGE_1$ retains little (1–2%) of the biological activity of $PGE_1$. 15-keto-$PGE_1$ is rapidly reduced at the $C_{13}$–$C_{14}$ position to form the most abundant metabolite in plasma, 13,14-dihydro,15-keto $PGE_1$ (DKH-$PGE_1$), which is biologically inactive. The majority of DKH-$PGE_1$ is further metabolized to smaller prostaglandin remnants that are cleared primarily by the kidney and liver. Between 60% and 90% of $PGE_1$ has bene shown to be metabolized after one pass through the pulmonary capillary beds.

Use of the present formulations either alone or in combination with various therapeutic agents overcomes all of these prior art deficiencies.

Regardless of the route of administration elected, the formulations of the present invention are formulated into pharmaceutically acceptable dosage forms by conventional methods known in the pharmaceutical art.

As discussed above, an effective but nontoxic amount of the system is employed in treatment. The dose regimen for administering drugs or treating various conditions, such as pain as described above, is selected in accordance with a variety of factors including the type, age, weight, sex, and medical condition of the subject, the severity of the pain, the route of administration and the particular complex or combination of drugs employed. Determination of the proper dose for a particular situation is within the skill of the art. Generally, treatment is initiated with smaller dosages which are less than the optimum doses of the compound. Thereafter, the dose is increased by small increments until the optimum effect under the circumstances is reached. For convenience, the total daily dosage may be divided and administered in portions during the day if desired. Generally, amounts of drug may vary from 0.0001% to about 75% by weight of the system when using topically with 0.5 to 5 ml concentrations and preferably in 1 to 3 ml amounts.

The formulations of this invention are particularly useful in the administration of drugs that could be previously administered only by injection.

The transdermal delivery system described herein offers a major alternative especially for those individuals who have a history of undesirable side-effects associated with irritation and/or pain from the injection. Also for those patients who have already suffered damage, the transdermal preparations described herein present a new way of providing effective treatment and relief of painful symptoms.

In addition to the negatively charged polymers, the transdermal polymer matrix must contain a non-ionic polymer which facilitates in retarding the absorption of the active drug through the skin and delays or slows down in animals natural absorption of the negatively charged polymer.

Without the presence of this component, the active drug would not be delivered transdermally into the site targeted for treatment at levels which are therapeutically effective. In addition to the non-ionic polymers described in this system, these materials are necessary to provide thorough penetration of skin layers including the epidermis, dermis and fatty tissue layers.

Particularly preferred nonionic polymers are cellulose derivatives and particularly those selected from the group consisting of carboxymethylcellulose sodium, hydroxyethyl cellulose, hydroxypropyl cellulose and mixtures thereof. These particular polymers have been found to possess exceptional ability to form sustained release matrix formulations when used in combination with a negatively charged polymer. Such polymers are generally employed in amounts of about 0.1% to about 1.5% and preferably about 0.5 to about 1.4%. Amounts above about 1.5% result in the formation of a solid gel when used with the negatively charged polymer. Amounts below about 0.1% have not been found suitable to prepare a storage stable product that has sustained drug release.

A particularly preferred HEC concentration is about 0.2% to about 1.0% by weight of the matrix.

A wide variety of medicaments which may be administered topically may be used in the delivery system according to this invention. These include drugs, without limitation, papaverine hydrochloride, phentolamine mesylate and prostaglandin E1, and mixtures thereof.

One particular criteria of the drug is that they must be solubilized in the polymer matrix solution in order to be topically administered.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLE 1

This example demonstrates the formation of a transdermal preparation of alprostadil.

The dosage range for the drug is between 2–3 ml.

| | |
|---|---|
| Aprostadil | 250 mcg |
| Sodium hyaluronate (HA) | 2.5% |
| Hydroxyethyl cellulose (HEC) | 0.7% |
| Methoxypolyethylene glycol (MPEG) | 10% |
| Benzyl alcohol | 1% |
| Water | Remainder |

BATCH SIZE 1000 ml

1. Into a sterilized glass vessel is added 1062.5 ml of sterile water which is stirred at 1500 to 2000 rpm. Slowly add 34.5 grams of HA, having a molecular weight of around 700,000 to 775,000 and a purity described above. Allow to stir for 16 to 20 hours until all of the HA polymer has dissolved into the water and a crystal-clear viscous solution has formed.
2. Prepare a 0.7% solution of HEC by adding 10.5 grams of the solid material under aseptic conditions to 250 ml of sterile water. Allow to dissolve for 1 to 2 hours while stirring at 1500 to 2000 rpm. Add the HEC solution to a sufficient amount of the HA solution and mix for 10 to 15 hours until a homogeneous solution is produced.
3. Carefully measure 100 ml of methoxypolyethylene glycol (MPEG) 10% into the mixture. RPM speeds should be increased for the mixture while this step is being performed to 2500 rpm. The resulting mixture thus formed should be allowed to mix at 2000 rpm for an additional 3 to 4 hours.
4. At this point 1% of benzol alcohol or 10 ml is added to the mixture. Again, the rpm speed is increased during this part of the procedure to 2500. The mixture should be allowed to mix for 3 to 5 hours at 2000 rpm.
5. Using safe techniques, 250 mg of aprostadil should be slowly added to the mixture. Again the rpm speed for the purpose of addition of drug should be increased to 2500, and the entire drug should be completed within 15 minutes.

The final mixture is clear with a slight tint following 15 to 20 hours of further mixing at 2000 rpm. The final product should be transferred, using aseptic technics, to 1–5 ml tubes.

When used, approximately 2 ml of matrix is applied to the exterior surface of the penis 10 to 15 minutes before intercourse. Alternatively, approximately 2 ml may be infused into the urethra 10 to 15 minutes before intercourse. Either technique results in the formation of an erection.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method for the treatment of erectile dysfunction in male animals, which comprises:

topically applying to a penis a therapeutically effective amount of a drug for treating impotency dispersed within a gelled composition comprising a polymer matrix which is suspended in a liquid medium; wherein the polymer matrix contains a negatively charged polymer blended with a nonionic polymer selected from the group consisting of hydroxyethyl cellulose, hydroxypropyl cellulose and mixtures thereof; and wherein the molar ratio of the negative charged polymer to the nonionic polymer is 1:0.5 to 4 and the negative charged polymer is present in amounts of about 2.0% to about 3.5% by weight.

2. The method of claim 1, wherein the negatively charged polymer is selected from the group consisting of glycosaminoglycans, mucopolysaccharides and mixtures thereof.

3. The method of claim 1, wherein the negatively charged polymer is chondroitin sulfate or hyaluronate salt of sodium, calcium, potassium or magnesium.

4. The method of claim 3, wherein the hyaluronate salt is the sodium salt and has a sulphonated ash content below about 15%, a protein content below about 5% and purity of at least 98%.

5. The method of claim 1, wherein the therapeutically effective amount of drug in the gelled composition is selected from the group consisting of papaverine, phentolamine, prostaglandin E1, and mixtures thereof.

6. The method of claim 1, wherein the therapeutically effective dose penetrates the exterior layers of the penis causing an erection without significantly modifying motor or sensory functions.

7. A gelled composition for treating impotency, which comprises: a therapeutically effective amount of a drug for treating impotency dispersed within a matrix containing a negatively charged polymer which is sodium hyaluronate blended with a nonionic polymer selected from the group consisting of hydroxyethyl cellulose, hydroxypropyl cellulose and mixtures thereof, wherein the molar ratio of the negative charged polymer to the nonionic polymer is 1:0.5 to 4 and the negative charged polymer is present in amounts of about 2.0% to about 3.0% by weight.

8. A method for the treatment of erectile dysfunction in male animals, which comprises:

injecting into the corpus cavernosa a therapeutically effective amount of a drug dispersed within a gelled composition comprising a polymer matrix which is suspended in a liquid medium; wherein the polymer matrix contains a negatively charged polymer blended with a nonionic polymer selected from the group consisting of hydroxyethyl cellulose, hydroxypropyl cellulose and mixtures thereof; and wherein the molar ratio of the negative charged polymer to the nonionic polymer is 1:0.5 to 4 and the negative charged polymer is present in amounts of about 2.0% to about 3.5% by weight.

9. The method of claim 8, wherein the negatively charged polymer material is selected from the group consisting of glycosaminoglycans, mucopolysaccharides and mixtures thereof.

10. The method of claim 8, wherein the negatively charged polymer material is chondroitin sulfate or hyaluronate salt of sodium, calcium, potassium or magnesium.

11. The method of claim 10, wherein the hyaluronate salt is the sodium salt and has a sulphated ash content below about 15%, a protein content below about 5% and purity of at least 98%.

12. The method of claim 8, wherein the therapeutically effective amount of drug in the gelled composition is selected from the group consisting of papaverine, phentolamine, prostaglandin E1, and mixtures thereof.

13. The method of claim 8, wherein the therapeutically effective dose penetrates the exterior layers of the penis causing an erection without significantly modifying motor or sensory functions.

14. A method for the treatment of erectile dysfunction in male animals, which comprises:

topically applying to a penis a therapeutically effective amount of a drug for treating impotency dispersed within a gelled composition comprising a polymer matrix which is suspended in a liquid medium; wherein the polymer matrix contains a negatively charged polymer blended with a nonionic polymer selected from the group consisting of hydroxyethyl cellulose, hydroxypropyl cellulose and mixtures thereof; and wherein the molar ratio of the negative charged polymer to the nonionic polymer is 1:0.5 to 4 and the negative charged polymer is present in amounts of about 2.0% to about 3.5% by weight;

and wherein the drug for treating impotency is prostaglandin $E_1$.

* * * * *